United States Patent
Grass

(10) Patent No.: US 8,329,796 B2
(45) Date of Patent: Dec. 11, 2012

(54) MIXTURES OF DIISONONYL ESTERS OF TEREPHTHALIC ACID, METHOD FOR THE PRODUCTION THEREOF AND USE THEREOF

(75) Inventor: Michael Grass, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 72 days.

(21) Appl. No.: 12/811,163

(22) PCT Filed: Dec. 3, 2008

(86) PCT No.: PCT/EP2008/066671
§ 371 (c)(1),
(2), (4) Date: Jun. 29, 2010

(87) PCT Pub. No.: WO2009/095126
PCT Pub. Date: Aug. 6, 2009

(65) Prior Publication Data
US 2010/0305255 A1     Dec. 2, 2010

(30) Foreign Application Priority Data

Jan. 28, 2008 (DE) .......................... 10 2008 006 400

(51) Int. Cl.
*C08K 5/09* (2006.01)
(52) U.S. Cl. ........................................ 524/321; 524/296
(58) Field of Classification Search ................... 524/321
See application file for complete search history.

(56) References Cited

U.S. PATENT DOCUMENTS

| | | |
|---|---|---|
| 6,355,711 B1 | 3/2002 | Godwin et al. |
| 6,437,170 B1 | 8/2002 | Thil et al. |
| 7,323,586 B2 | 1/2008 | Wiese et al. |
| 7,323,588 B2 | 1/2008 | Grass et al. |
| 7,638,568 B2 | 12/2009 | Grass et al. |
| 2004/0238787 A1* | 12/2004 | Wiese et al. ............ 252/182.28 |
| 2005/0049341 A1 | 3/2005 | Grass et al. |
| 2006/0041167 A1* | 2/2006 | Grass et al. .................. 562/509 |
| 2006/0167151 A1* | 7/2006 | Grass et al. .................. 524/285 |
| 2007/0179229 A1 | 8/2007 | Grass |
| 2008/0188601 A1 | 8/2008 | Grass et al. |

FOREIGN PATENT DOCUMENTS

WO     00 63151     10/2000

OTHER PUBLICATIONS

Beeler, A. Don "Terephthalate Esters a New Class of Plasticizers for Polyvinyl Chloride", SPE Annual Technical Conference and Exhibition, pp. 613-615, XP008040735, (Apr. 26, 1976).

* cited by examiner

*Primary Examiner* — Hui Chin
(74) *Attorney, Agent, or Firm* — Oblon, Spivak, McClelland, Maier & Neustadt, L.L.P.

(57) ABSTRACT

The invention relates to mixtures of diisononyl esters of terephthalic acid, characterized in that the isomeric nonyl radicals bound in the ester mixture have an average degree of branching of 1.0 to 2.2. Said mixtures can advantageously be used as softeners or part of a softener composition in plastics or plastic components.

19 Claims, 1 Drawing Sheet

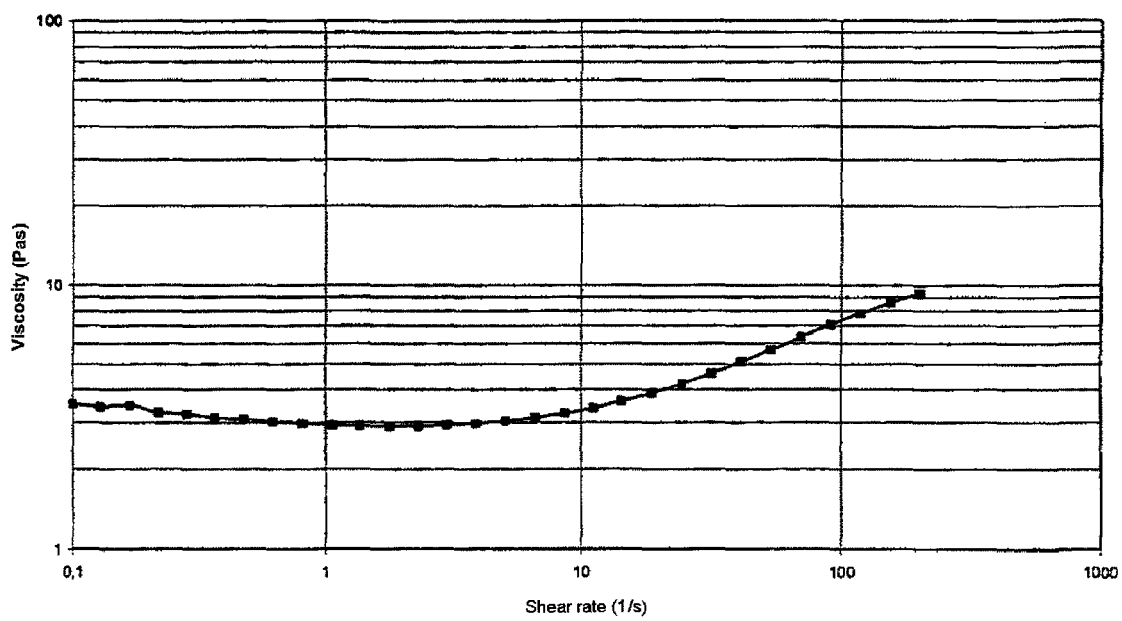

MIXTURES OF DIISONONYL ESTERS OF TEREPHTHALIC ACID, METHOD FOR THE PRODUCTION THEREOF AND USE THEREOF

The invention relates to diisononyl terephthalate mixtures, i.e. diisononyl esters of terephthalic acid, which take the form of isomer mixtures, in which the isomeric nonyl moieties in the ester mixture have a particular degree of branching. The present invention also relates to the use of these mixtures and to a process for their production.

Polyvinyl chloride (PVC) is one of the polymers of greatest commercial importance. It is widely used in the form of either rigid or flexible PVC.

To produce flexible PVC, plasticizers are added to the PVC, and those used in most cases are phthalic esters, in particular di-2-ethylhexyl phthalate (DEHP), diisononyl phthalate (DINP) and diisodecyl phthalate (DIDP).

Discussions about reproduction-toxicity effects have in some cases already led to an increased level of identification marking under hazardous materials legislation, and have also led to limitations on use in toys for toddlers, and it therefore has to be assumed that the use of these phthalates will reduce markedly in the future, particularly in sensitive applications, such as food-or-drink packaging and medical applications. There is therefore a need for plasticizers which are not subject to identification-marking requirements and which can be used as replacement for DEHP or for DINP, and which can be produced from raw materials of which large quantities are available worldwide.

Alongside phthalic acid, another substance available in large quantities, with an estimated annual production in the region of millions of tons, is terephthalic acid (PTA) and, respectively, the derivative dimethyl terephthalate (DMT). An example of a product produced on a large scale from terephthalic acid is polyethylene terephthalate (PET). However, only one monomeric ester of terephthalic acid has hitherto achieved some degree of industrial significance as plasticizer for PVC, namely di-2-ethylhexyl terephthalate (DEHT or DOTP).

According to James L. Cooper (in the paper: "An Alternative to DEHP in Plasticized PVC", delivered to the Vinyl Formulators Division, $16^{th}$ Annual Compounding Conference, Harrah's/Harvey's Resort, Lake Tahoe, Nev., 17-19 Jul. 2005) diesters of phthalic acid, in particular di-2-ethylhexyl phthalates, are metabolized differently from the diesters of terephthalic acid. During degradation in organisms, the terephthalates are first completely hydrolyzed to give alcohol and terephthalic acid, whereas the phthalates are only hydrolyzed to give the monoester. These monoesters, or subsequent products produced from the same by subsequent oxidative reactions, have been identified in laboratory studies as toxicologically active substances. Because di-2-ethylhexyl phthalate and di-2-ethylhexyl terephthalate are metabolized differently, di-2-ethylhexyl terephthalate has, according to James L. Cooper, markedly lower toxicity than di-2-ethylhexyl phthalate.

It can therefore be assumed that other plasticizers likewise based on terephthalic esters likewise undergo entirely similar complete hydrolysis to terephthalic acid during degradation, and that these terephthalates therefore likewise have lower toxicity than the corresponding phthalates.

An advantage over the cyclohexanedicarboxylic esters which have likewise been proposed as phthalate alternatives and which are accessible via ring-hydrogenation of the corresponding phthalates, is that the terephthalates, like the phthalates, can be produced via a one-stage esterification reaction starting from readily available raw materials, with no need for any additional hydrogenation stage. Conversion of the production process to terephthalates therefore results in only a low level of requirement for necessary changes to production plants, and no capital expenditure on plant for a hydrogenation stage.

There are few descriptions in the literature of esters of terephthalic acid and isononanol, i.e. a mixture of branched and, if appropriate, linear nonyl alcohol(s), and nor have these been marketed as plasticizers hitherto.

U.S. Pat. No. 2,628,207 describes terephthalic esters as plasticizers, and those of the $C_8$ alcohols are described in that document as particularly preferred, since they are said to represent the optimum of opposite effects associated with rising molar mass, comprising plasticizing action and low volatility. No information is revealed relating to diisononyl terephthalates.

Soc. Plast. Eng., Tech. Pap (1976), 22, 613-615 says that terephthalic esters have much greater tendency towards crystallization than the corresponding phthalic esters and are in some cases also incompatible with PVC. In the case of terephthalic esters whose average chain length is 9 carbon atoms, it is said that a minimum proportion of 30% of branched alcohols is necessary in order to obtain liquid, PVC-compatible plasticizers. In relation to performance properties, it is said that the behaviour of terephthalic esters is generally similar to that of the corresponding phthalic esters whose side chains are longer by one carbon atom.

A number of other publications, such as DE 199 27 978, merely mention diisononyl terephthalates, or in a few cases also mention the possibility of use as plasticizer, an example being JP 2001240844, where the use as plasticizer in polyurethane systems is described. However, there has never been an explicit study of performance characteristics, and in particular these have not been studied as a function of the constitution of the isononyl side chain or the degree of branching.

Starting from the known prior art, the object of the present invention consisted in provision of diisononyl terephthalates which have good suitability as plasticizers, in particular for the plasticizing of PVC.

The action of a plasticizer consists in reducing the glass transition temperature of the plastic to be plasticized sufficiently that it retains adequate flexibility at service temperatures. The intention is therefore that the glass transition temperature of the material be below the service temperature. Suitable diisononyl terephthalates should therefore exhibit the lowest possible glass transition temperature. The glass transition temperature for DEHP will be used as guideline value here and is about −80° C. (determined by means of differential scanning calorimetry, DSC).

A particular intention was therefore, while permitting certain tolerances, to find mixtures of isomeric dinonyl terephthalates which give a glass transition temperature below −70° C., ideally below −80° C.

Technical experience teaches us that the glass transition temperature generally becomes lower as the amount of branching of the alcohol content in the ester mixture decreases. Di-n-nonyl terephthalate should actually therefore be the most suitable substance.

However, when n-nonanol was used for the production of the corresponding dinonyl terephthalate it was found that the resultant ester has only limited usefulness as plasticizer for PVC, since it is solid at room temperature (see comparative example 4) and therefore is unsuitable as plasticizer for plastisol applications, which in terms of quantity are the most important. No glass transition temperature for this ester could be detected by means of DSC (no amorphous fractions).

Equally, esterification of the triply branched substance 3,5,5-trimethylhexanol, which is obtained by hydroformylation of diisobutene, also gives only a terephthalic ester which is solid at room temperature. The statement in Soc. Plast. Eng., Tech. Pap (1976), 22, 613-615 to the effect that at least 30% of the C9 alcohols have to be branched in order to avoid crystallization is therefore not entirely correct.

Surprisingly, it has now been found that mixtures of isononyl terephthalates which comprise at least two constitutionally different nonyl moieties and whose average degree of branching is from 1.0 to 2.2 are liquid even at low temperatures down to about −70° C. and exhibit glass transition temperatures below −70° C. These isononyl terephthalates therefore have particularly good suitability as plasticizers, in particular as plasticizers for PVC.

The invention therefore provides mixtures of diisononyl esters of terephthalic acid in which the average degree of branching of the isomeric nonyl moieties in the ester mixture is from 1.0 to 2.2.

The invention further provides a process for the production of mixtures of diisononyl esters of terephthalic acid, characterized in that the production process uses a mixture of isomeric nonanols whose average degree of branching is from 1.0 to 2.2.

The invention also provides the use of the inventive mixtures as plasticizer or part of a plasticizer composition in plastics or components of plastics, or as additive in paints or in coatings, or in adhesives or components of adhesives, or in sealing compositions, or as solvent.

Finally, the invention provides plastics and plastics compositions, in particular based on PVC, PVB or PAMA, which comprise the inventive mixtures of diisononyl esters of terephthalic acid, and also provides plastics products produced from these compositions.

The inventive mixtures of diisononyl esters of terephthalic acid are characterized in that the degree of branching of the isononyl moieties of the diisononyl esters present in the mixture is from 1.0 to 2.2, preferably from 1.1 to 2.1. A particularly preferred degree of branching is from 1.1 to 2.0, and in particular from 1.2 to 1.5.

The isononyl moieties here are based on primary nonyl alcohols.

$^1$H NMR methods or $^{13}$C NMR methods can be used to determine the average degree of branching of the isononyl moieties in the terephthalic diester mixture. According to the present invention, it is preferable to determine the degree of branching with the aid of $^1$H NMR spectroscopy on a solution of the diisononyl esters in deuterochloroform ($CDCl_3$). The spectra are recorded by way of example by dissolving 20 mg of substance in 0.6 ml of $CDCl_3$ (comprising 1% by weight of TMS) and charging the solution to an NMR tube whose diameter is 5 mm. Both the substance to be studied and the $CDCl_3$ used can first be dried over molecular sieve in order to exclude any errors in the values measured due to possible presence of water. The method of determination of the degree of branching is advantageous in comparison with other methods for the characterization of alcohol moieties, described by way of example in WO 03/029339, since water contamination in essence has no effect on the results measured and their evaluation. In principle, any commercially available NMR equipment can be used for the NMR-spectroscopic studies. The present NMR-spectroscopic studies used Avance 500 equipment from Bruker. The spectra were recorded at a temperature of 300 K using a delay of d1=5 seconds, 32 scans, a pulse length of 9.7 μs and a sweep width of 10 000 Hz, using a 5 mm BBO (broad band observer) probe head. The resonance signals are recorded in comparison with the chemical shifts of tetramethylsilane (TMS=0 ppm) as internal standard. Comparable results are obtained with other commercially available NMR equipment using the same operating parameters.

The resultant $^1$H NMR spectra of the mixtures of diisononyl esters of terephthalic acid have, in the range from 0.5 ppm as far as the minimum of the lowest value in the range from 0.9 to 1.1 ppm, resonance signals which in essence are formed by the signals of the hydrogen atoms of the methyl group(s) of the isononyl groups. The signals in the range of chemical shifts from 3.6 to 4.4 ppm can essentially be attributed to the hydrogen atoms of the methylene group adjacent to the oxygen of the alcohol or of the alcohol moiety. The results are quantified by determining the area under the respective resonance signals, i.e. the area included between the signal and the base line. Commercially available NMR equipment has devices for integrating the signal area. In the present NMR-spectroscopic study, integration used "xwinnmr" software, version 3.5. The integral value of the signals in the range from 0.5 as far as the minimum of the lowest value in the range from 0.9 to 1.1 ppm is then divided by the integral value of the signals in the range from 3.6 to 4.4 ppm to give an intensity ratio which states the ratio of the number of hydrogen atoms present in a methyl group to the number of hydrogen atoms present in a methylene group adjacent to an oxygen atom. Since there are three hydrogen atoms per methyl group and two hydrogen atoms are present in each methylene group adjacent to an oxygen atom, each of the intensities has to be divided by 3 and, respectively, 2 in order to obtain the ratio of the number of methyl groups to the number of methylene groups adjacent to an oxygen atom, in the isononyl moiety. Since a linear primary nonanol which has only one methyl group and one methylene group adjacent to an oxygen atom contains no branching and accordingly must have a degree of branching of 0, the quantity 1 then has to be subtracted from the ratio.

The degree of branching B can therefore be calculated from the measured intensity ratio in accordance with the following formula:

$$B = 2/3 * I(CH_3)/I(OCH_2) - 1$$

B here means degree of branching, $I(CH_3)$ means area integral essentially attributed to the methyl hydrogen atoms, and $I(OCH_2)$ means area integral for the methylene hydrogen atoms adjacent to the oxygen atom.

The nature and number of the alcohol moieties present in the diisononyl ester mixtures can also be determined by saponifying the ester in basic solution and then analyzing the alcohol by GC. Care has to be taken here that the GC conditions (in particular column material and column dimensions, and also temperature profile) permit separation of the alcohols into the individual isomers.

The isomeric nonanols or isononanol mixtures to be used in the inventive process for the production of these mixtures of diisononyl esters of terephthalic acid can generally be produced by hydroformylation of octenes, which in turn can be produced in various ways. The raw material generally used for the production of the octenes comprises industrial $C_4$ streams, which initially can comprise all of the isomeric $C_4$ olefins, alongside the saturated butanes and sometimes impurities such as $C_3$ and $C_5$ olefins and acetylenic compounds. Oligomerization of this olefin mixture gives mainly isomeric octene mixtures, alongside higher oligomers such as $C_{12}$ and $C_{16}$ olefin mixtures. These octene mixtures, from which the higher oligomers have preferably been removed by distillation, are hydroformylated to give the corresponding aldehydes, and then hydrogenated to give the alcohol. The constitution, i.e. the isomer distribution of these technical nonanol mixtures, depends on the starting material and on the oligomerization process and hydroformylation process.

Other examples of octene mixtures that can be used are those obtained by way of what is known as the polygas process, in which $C_3/C_4$ mixtures are oligomerized on a solid acidic catalyst, preferably on a solid phosphoric acid catalyst (SPA process). This process is described inter alia in the documents U.S. Pat. No. 6,284,938, U.S. Pat. No. 6,080,903, U.S. Pat. No. 6,072,093, U.S. Pat. No. 6,025,533, U.S. Pat. No. 5,990,367, U.S. Pat. No. 5,895,830, U.S. Pat. No. 5,856, 604, U.S. Pat. No. 5,847,252 and U.S. Pat. No. 5,081,086. The nonanols obtained by these processes generally also comprise octanols and decanols, and sometimes also undecanols, and the average chain length here can therefore deviate from 9 carbon atoms. This has no effect on the determination of the degree of branching B by the abovementioned method, however.

Because of the raw material used, and for process reasons, the constitution of this $C_9$-rich $C_5$-$C_{11}$ alcohol mixture is markedly more complex, and attribution of the individual peaks in the corresponding gas chromatograms cannot be achieved without enormous additional cost. A characteristic of this mixture is that the proportion of n-nonanol is generally markedly below two percent.

A distribution in typical products of this type has from 2 to 6% of octanols, from 70 to 78% of nonanols, from 15 to 25% of decanols and at most 2% of undecanols. The boiling range (start of boiling to dry point) is from 202° C. to 219° C. at atmospheric pressure. The EU Risk Assessment on diisononyl phthalate from the polygas process (DINP 1, CAS no. 68515-48-0, Jayflex DINP) says that the alcohol used for this purpose is composed of from 5 to 10% by weight of methylethylhexanols, from 45 to 55% by weight of dimethylheptanols, from 5 to 20% by weight of methyloctanols, from 0 to 1% by weight of n-nonanol and from 15 to 25% of decanols.

One commercially available embodiment of this type of isononanol mixture, which can be used for the production of the diisononyl terephthalates used according to the invention, has the following constitution (producer: Exxon):
  from 1.73 to 3.73 mol % of 3-ethyl-6-methyl-hexanol;
  from 0.38 to 1.38 mol % of 2,6-dimethylheptanol;
  from 2.78 to 4.78 mol % of 3,5-dimethylheptanol;
  from 6.30 to 16.30 mol % of 3,6-dimethylheptanol;
  from 5.74 to 11.74 mol % of 4,6-dimethylheptanol;
  from 1.64 to 3.64 mol % of 3,4,5-trimethylhexanol;
  from 1.47 to 5.47 mol % of 3,4,5-trimethylhexanol, 3-methyl-4-ethylhexanol and 3-ethyl-4-methylhexanol;
  from 4.00 to 10.00 mol % of 3,4-dimethylheptanol;
  from 0.99 to 2.99 mol % of 4-ethyl-5-methylhexanol and 3-ethylheptanol;
  from 2.45 to 8.45 mol % of 4,5-dimethylheptanol and 3-methyloctanol;
  from 1.21 to 5.21 mol % of 4,5-dimethylheptanol;
  from 1.55 to 5.55 mol % of 5,6-dimethylheptanol;
  from 1.63 to 3.63 mol % of 4-methyloctanol;
  from 0.98 to 2.98 mol % of 5-methyloctanol;
  from 0.70 to 2.70 mol % of 3,6,6-trimethylhexanol;
  from 1.96 to 3.96 mol % of 7-methyloctanol;
  from 1.24 to 3.24 mol % of 6-methyloctanol;
  from 0.01 to 3 mol % of n-nonanol;
  from 25 to 35 mol % of other alcohols having 9 and 10 carbon atoms;
  where the entirety of the components mentioned gives 100 mol %.

The degree of branching of nonanol mixtures of this constitution is generally from 1.4 to 2.2 according to the abovementioned method, in particular from 1.5 to 2.0, and particularly typically from 1.6 to 1.9.

Particularly preferred mixtures which can be used in the inventive process and comprise isomeric nonanols are those obtainable via hydroformylation of a mixture of isomeric octenes and subsequent or simultaneous hydrogenation. The mixture of isomeric octenes here is obtained by bringing a hydrocarbon mixture comprising butenes into contact with an oligomerization catalyst, in particular with a catalyst formally comprising nickel oxide. The proportion of isobutene in the hydrocarbon mixture is preferably smaller than 20% by weight, with preference smaller than 10% by weight, particularly preferably smaller than 5% by weight, very particularly preferably smaller than 3% by weight, with particular preference smaller than 1% by weight, preferably from 0.01 to 1% by weight and with particular preference from 0.05 to 0.5% by weight, based on the butenes. The preparation of isomeric octenes via oligomerization of essentially linear butenes on supported nickel catalysts is known by way of example as the OCTOL process, which is described by way of example in EP 0 395 857 or EP 1 029 839.

The mixtures of isomeric octenes are then fed to a hydroformylation process. The hydroformylation process can take place in the presence of modified or unmodified cobalt catalysts or modified or unmodified rhodium catalysts. The hydroformylation process preferably takes place in the presence of unmodified cobalt compounds. The hydroformylation process is usually followed by a hydrogenation process. These hydroformylation/hydrogenation processes are known by way of example from EP 0 850 905 and EP 1 172 349. The hydroformylation process can also take place in the presence of rhodium catalysts. These hydroformylation processes are well known. Specific processes for hydroformylation which have particularly good suitability for production of mixtures which can be used in the inventive process and which comprise isomeric nonanols are described by way of example in WO 2004/020380 or DE 103 27 435. The processes described in those documents are carried out in the presence of cyclic carbonic esters.

It can also be advantageous, as described in EP 1 172 349, to begin by fractionating the mixture of isomeric octenes, prior to feed to the hydroformylation process. This method can give octene fractions which have particularly good suitability for the production of mixtures which can be used in the inventive process and which comprise isomeric nonanols. The fractions can then be used in a relatively simple manner to obtain a mixture of isomeric octenes via mixing of suitable fractions, and this mixture is suitable for the production of mixtures of isomeric nonanols for use in the inventive process.

The following is an example (producer: Evonik OXENO) of the constitution of nonanol mixtures which are produced in this way and are available commercially, and are particularly suitable for the production of the inventive diisononyl terephthalates:
  from 2.0 to 12.0 mol % n-nonanol;
  from 12.0 to 30.0 mol % 6-methyloctanol;
  from 12.0 to 30.0 mol % 4-methyloctanol;
  from 1.0 to 7.0 mol % 2-methyloctanol;
  from 5.7 to 11.7 mol % 3-ethylheptanol;
  from 1.0 to 4.5 mol % 2-ethylheptanol;
  from 0.5 to 4.0 mol % 2-propylhexanol;
  from 8.0 to 22.0 mol % 4,5-dimethylheptanol;
  from 5.0 to 16.0 mol % 2,5-dimethylheptanol;
  from 1.5 to 4.5 mol % 2,3-dimethylheptanol;

from 1.0 to 7.5 mol % 3-ethyl-4-methylhexanol;
from 0.5 to 6.0 mol % 2-ethyl-4-methylhexanol;
from 0.2 to 6.5 mol % of other primary alcohols having 9 carbon atoms;
where the entirety of the components mentioned gives 100 mol %.

The degree of branching of nonanol mixtures of this constitution, determined in accordance with the abovementioned method, is generally from 1.1 to 1.4, in particular from 1.2 to 1.3.

In variants from the OCTOL process using catalysts comprising nickel, by way of example, catalysts comprising Ti or comprising Zr are used for the production of the octene mixture. These alternative variants and in particular the catalysts are described by way of example in EP 1 171 413.

The following is an example (producer: BASF) of the constitution of nonanol mixtures which are produced in this way and are available commercially, and are particularly suitable for the production of the inventive diisononyl terephthalates:

from 6.0 to 16.0 mol % n-nonanol;
from 12.8 to 28.8 mol % 6-methyloctanol;
from 12.5 to 28.8 mol % 4-methyloctanol;
from 2.0 to 7.3 mol % 2-methyloctanol;
from 5.7 to 11.7 mol % 3-ethylheptanol;
from 1.3 to 3.9 mol % 2-ethylheptanol;
from 1.0 to 3.7 mol % 2-propylhexanol;
from 3.2 to 16.0 mol % 4,5-dimethylheptanol;
from 4.0 to 16.0 mol % 2,5-dimethylheptanol;
from 1.0 to 4.0 mol % 2,3-dimethylheptanol;
from 1.0 to 7.5 mol % 3-ethyl-4-methylhexanol;
from 1.0 to 5.0 mol % 2-ethyl-4-methylhexanol;
from 0.5 to 6.5 mol % of other alcohols having 9 carbon atoms;
where the entirety of the components mentioned gives 100 mol %.

The degree of branching of isononanol mixtures of this constitution, determined in accordance with the abovementioned method, is generally from 1.0 to 1.4, in particular from 1.2 to 1.3.

However, the mixture of isomeric nonanols used in the inventive process can also comprise a mixture obtained via mixing of isomerically pure nonanols and/or fractions of a plurality of isomeric nonanols. A large number of isomerically pure nonanols is commercially available. Nonanol mixtures or nonanol fractions are equally commercially available which do not have the properties preferred for the inventive process. Simple mixing of these isomerically pure nonanols with nonanol mixtures can produce mixtures of nonanols which have the desired average degrees of branching and which provide terephthalic diester mixtures with the properties demanded.

The isononyl alcohol mixtures to be used ideally comprise no more than from 0.0001 to 10 mol % of 3,5,5-trimethylhexanol. The mixture preferably comprises less than 5 mol %, in particular less than 1 mol % and particularly preferably less than 0.5 mol %, of 3,5,5-trimethylhexanol.

The proportion of n-nonanol in the isononyl alcohol mixture to be used is from 0.001 to 20 mol %, preferably from 1 to 18 mol % and particularly preferably from 5 to 15 mol %.

The contents of 3,5,5-trimethylhexanol and of n-nonanol in the alcohol mixture can be determined conventionally by gas-chromatographic analysis methods (GC).

Nonyl alcohol mixtures obtained via saponification of the inventive diisononyl esters preferably comprise from 0.001 to 20 mol %, preferably from 0.5 to 18 mol %, particularly preferably from 6 to 16 mol %, of unbranched nonanols (i.e. n-nonanol). These mixtures moreover comprise from 5 to 90 mol %, preferably from 10 to 80 mol %, particularly preferably from 45 to 75 mol %, of nonanols having branching, and also from 5 to 70 mol %, preferably from 10 to 60 mol %, particularly preferably from 15 to 35 mol % of doubly branched nonanols, and, finally, from 0.1 to 15 mol %, preferably from 0.1 to 8 mol %, particularly preferably from 0.1 to 5 mol %, of triply branched nonanols. Alongside this, these nonanol mixtures can also comprise from 0 to 40 mol %, preferably from 0 to 30 mol %, particularly preferably from 0.1 to 6.5% by weight, of other components. Other components are generally octanols, decanols or nonanols more than triply branched, where the entirety of all of the components mentioned gives 100 mol %.

The inventive mixtures of diisononyl terephthalates can be produced by the following methods:
 a) by transesterification of terephthalic esters having alkyl moieties which have fewer than 8 carbon atoms, using a mixture of isomeric primary nonanols
 b) by esterification of terephthalic acid, using a mixture of primary nonanols
 c) by complete or partial transesterification of a dinonyl terephthalate or of a mixture of isomeric dinonyl terephthalates, using a primary nonanol or using a mixture of primary nonanols
 d) by mixing of isomerically pure nonyl terephthalates with one another, mixing of an isomerically pure nonyl terephthalate with a mixture of nonyl terephthalates, or mixing of two or more mixtures of dinonyl terephthalates.

The inventive mixtures of isomeric dinonyl terephthalates are preferably produced by methods a) and b).

If diisononyl terephthalate is produced by transesterification, a preferred starting material is dimethyl terephthalate (DMT), which is produced on a large industrial scale.

The transesterification process is carried out catalytically, for example using bases or Lewis acids or Brönstedt acids as catalyst. Irrespective of which catalyst is used, a temperature-dependent equilibrium always becomes established between the starting materials (dialkyl terephthalate and isononanols) and the products (diisononyl terephthalates and alcohol liberated from the dialkyl terephthalate used). In order to shift the equilibrium in favour of the inventive terephthalic ester, it can be advantageous to use distillation to remove, from the reaction mixture, the alcohol deriving from the starting ester.

Again, in this embodiment of the inventive process it can be advantageous to use an overall excess of the alcohol. The excess used of the starting alcohol is preferably from 5 to 50%, in particular from 10 to 30%, of the molar amount needed for formation of the inventive dialkyl terephthalate.

The transesterification catalysts used can comprise acids, such as sulphuric acid, methanesulphonic acid or p-toluenesulphonic acid, or metals or compounds of these. Examples of suitable metals or compounds of these are tin, titanium and zirconium, which are used in the form of finely divided metals or advantageously in the form of their salts, or as oxides or in the form of soluble organic compounds. Unlike the catalysts based on protic acids, the metal catalysts are high-temperature catalysts whose full activity is often achieved only above 180° C. It can be advantageous to use these metal catalysts based on metals or compounds of these, since it has been found that these catalysts are better than catalysts based on protic acids in leading to less formation of by-products, such as olefins from the alcohol used. Examples of metal catalysts whose use is particularly preferred are tin powder, stannous oxide, stannous oxalate, titanic esters, such as tetraisopropyl orthotitanate or tetrabutyl orthotitanate, and also zirconium esters, such as tetrabutyl zirconate. It is also possible to use basic catalysts, such as oxides, hydroxides, hydrogen carbonates, carbonates or alcoholates of alkali metals or of alkaline earth metals. Among this group, preference is given to use of alcoholates, such as sodium methoxide. Alcoholates can also be produced in situ from an alkali metal and a nonanol or an isononanol mixture. It is particularly preferable to use alcoholates whose alcohol moiety is identical with that of one of the alcohols involved in the reaction.

The catalyst concentration can be varied widely and in particular as a function of the nature of the catalyst. The catalyst concentration is preferably from 0.005 to 2.0% by weight, based on the reaction mixture. The ideal concentrations for each catalyst can readily be determined by preliminary experiments and are obtained from a compromise between minimum catalyst usage (i.e. cost) and maximum reaction rate. In the case of the particularly preferred titanium compound tetrabutyl orthotitanate, the preferred concentration is by way of example in the range from 0.05 to 1% by weight, based on the dialkyl terephthalate used.

The transesterification process is preferably carried out at a temperature of 100 and 220° C. The temperature is particularly preferably selected to be sufficiently high to permit distillative removal, from the reaction mixture, of the alcohol deriving from the starting ester, at the prescribed pressure.

These crude ester mixtures can be worked up in the same way as those produced by the esterification of terephthalic acid described hereinafter.

Any of the known processes can be used for the production of the inventive mixtures of dinonyl terephthalate by esterification of terephthalic acid using a mixture of primary nonanols. However, the esterification step preferably takes place by a process in which the water of reaction is removed by azeotropic distillation with the alcohol and the amount of liquid removed from the reaction by the azeotropic distillation is completely or to some extent replaced by the alcohol. The term amount of liquid is used hereinafter for the volume of liquid removed from the reaction by azeotropic distillation, mainly composed of water of reaction and alcohol. Complete replacement of the amount of liquid removed is preferred. This can by way of example be achieved by level-controlled feed of alcohol into the reactor. For technical reasons it can be difficult or impossible to achieve complete replacement of the amount of liquid removed. In these cases, the amount of liquid removed is replaced only partially, for example only the alcohol being replaced, while the amount of water of reaction removed is not replaced, but the proportion replaced is always more than 90%, preferably from 95 to 98%.

It can also be necessary to return, into the reactor, more than the amount of liquid removed by distillation, i.e. not only the amount of alcohol removed but also the water of reaction is replaced and moreover further alcohol is added. In this embodiment of the esterification process, the proportion of the amount of liquid removed that is replaced by alcohol is from 110 to 100%, preferably from 105 to 100%.

An advantage of this embodiment of the esterification process is that the reaction rate is increased in comparison with known batch processes. The result can be a shorter cycle time, thus achieving higher space-time yield.

The esterification process carried out can be an autocatalyzed or catalyzed reaction. Esterification catalysts which can be used are Lewis acids and Brönstedt acids or organometallic substances, which do not necessarily have to act as an acid. Preferred esterification catalysts are alcoholates, and carboxylic salts or chelate compounds of titanium or zirconium, where the catalyst molecule can comprise one or more metal atoms. In particular, tetra(isopropyl) orthotitanate and tetra(butyl) orthotitanate are used.

The esterification process is preferably carried out in a reaction vessel in which the reaction mixture can be intimately mixed with the aid of a stirrer or of a circulating pump. The starting materials and the catalyst can be charged to the reactor simultaneously or in succession. If one of the starting materials is solid at the charging temperature, it is advantageous to use the liquid starting component as initial charge. Solid starting materials can be fed in the form of powder, granules, crystals or melt. In order to shorten the batch time, it is advisable to start heating during charging. The catalyst can be introduced in pure form or as solution, preferably dissolved in one of the starting materials, at the start or only after the reaction temperature has been reached.

The alcohol to be reacted serves as entrainer and can be used in stoichiometric excess. An excess of from 5 to 50%, particularly preferably from 10 to 30%, is preferably used.

The catalyst concentration depends on the nature of the catalyst. In the case of the titanium compounds whose use is preferred, this is from 0.005 to 1.0% by weight, based on the reaction mixture, in particular from 0.01 to 0.3% by weight.

When titanium catalysts are used, the reaction temperatures are from 160° C. to 270° C. The ideal temperatures are dependent on the starting materials and on the progress of the reaction, and on the catalyst concentration. They can readily be determined experimentally for any particular case. Higher temperatures increase the reaction rates and favour side-reactions, for example water cleavage from alcohols or formation of coloured by-products. For removal of the water of reaction, a requirement is that the alcohol can be removed from the reaction mixture by distillation. The desired temperature or the desired temperature range can be adjusted via the pressure in the reaction vessel.

The amount of liquid to be returned to the reaction can be composed to some extent or entirely of alcohol obtained via work-up of the azeotropic distillate. It is also possible to carry out the work-up at a later juncture and to use, entirely or to some extent, fresh alcohol, i.e. alcohol provided in a feed vessel, to replace the amount of liquid removed. In other embodiments of the esterification process, the liquid removed is worked up to give the alcohol, preferably to give the pure alcohol.

Once the reaction has ended, the reaction mixture, which is composed essentially of full ester (desired product) and of excess alcohol, comprises not only the catalyst and/or products produced from the catalyst but also small amounts of ester carboxylic acid(s) and/or unreacted carboxylic acid. For work-up of these crude ester mixtures, the excess alcohol is removed, the acidic compounds are neutralized, and the catalyst is destroyed, and the solid by-products produced in the process are removed. Most of the alcohol is removed here by distillation at atmospheric pressure or in vacuo. The final traces of the alcohol can by way of example be removed by steam distillation, in particular in the temperature range from 120 to 225° C. Removal of the alcohol can by way of example be the first or last step of the work-up.

The neutralization of the acidic substances, such as carboxylic acids or ester carboxylic acids, or, if appropriate, of the acidic catalysts, can take place via addition of basic compounds of the alkali metals and of the alkaline earth metals. These can be used in the form of their carbonates, hydrogen carbonates or hydroxides. The neutralizing agent can be used in solid form or preferably as solution, in particular as aqueous solution. The neutralization can be carried out immediately after the esterification reaction has ended, or after removal of most of the excess alcohol by distillation. Preference is given to neutralization using aqueous sodium hydroxide immediately after ending of the esterification reaction at temperatures above 150° C. The water introduced with the aqueous sodium hydroxide can then be removed by distillation together with alcohol.

Further details of suitable esterification processes which can be used as esterification step in the inventive process can be found by way of example in EP 1 186 593 and EP 1 300 388.

It can be particularly advantageous to carry out the esterification process in the manner described in DE 10 2005 021 075.9.

Even at boiling point, terephthalic acid is only sparingly soluble in the alcohol(s) to be used for the esterification process, and superatmospheric pressure can therefore be used to increase solubility and thus increase reaction rate. Otherwise, batch times can become very prolonged.

If DMT is used for the transesterification process, these problems do not arise. Starting from DMT, it is generally possible to obtain the corresponding terephthalate in shorter batch times than with terephthalic acid as starting material. It is therefore particularly preferable to produce the inventive diisononyl terephthalates by transesterification starting from DMT.

The inventive diisononyl terephthalate mixtures can be used advantageously as plasticizer or part of a plasticizer composition in plastics or components of plastics, or as additive in paints or in coatings, or in adhesives or in components of adhesives, or in sealing compositions, or as solvent.

The advantages of the inventive diisononyl terephthalate mixtures here are as follows:

The inventive diisononyl terephthalates are more versatile than dialkyl terephthalates having 9 C atoms in the side chain which are isomerically pure, e.g. di-n-nonyl terephthalate and di-3,5,5-trimethylhexyl terephthalate, since they are liquid at room temperature and can therefore also be used in plastisol processes, which are quantitatively significant, and in which room-temperature application is possible only by using a liquid plasticizer phase. Since they are liquid even at low temperatures down to about −70° C., and exhibit glass transition temperatures below −70° C. or in some cases can reach temperatures as low as the glass transition temperature without any crystallization at all, they can moreover be pumped without difficulty even at very low temperatures and are therefore preferably suitable for industrial applications of this type.

When compared with the corresponding dialkyl terephthalates with a higher degree of branching, they have lower viscosity, which is advantageous for processing in the plastisol process. When compared with the less branched isomers, they have better compatibility with the polymer.

The inventive diisononyl terephthalate mixtures or else the mixtures of these with plastics, preference being given here to PVC, PVB and PAMA, can also comprise further compounds which can be used as plasticizers. Among these compounds, which are particularly preferably esters, are by way of example the following:
dialkyl phthalates, preferably having from 4 to 13 carbon atoms in the alkyl chain; trialkyl trimellitates, preferably having from 6 to 10 carbon atoms in the side chain; dialkyl adipates, preferably having from 6 to 10 carbon atoms; dialkyl terephthalates, in each case preferably having from 4 to 8 carbon atoms, in particular from 4 to 5 carbon atoms, in the side chain;
1,2-cyclohexanediacid alkyl esters, 1,3-cyclohexanediacid alkyl esters and 1,4-cyclohexanediacid alkyl esters, preference being given here to 1,2-cyclohexanediacid alkyl esters, in each case preferably having from 4 to 10 carbon atoms in the side chain; dibenzoic esters of glycols; alkylsulphonic esters of phenol preferably having an alkyl moiety which comprises from 8 to 22 carbon atoms; polymer plasticizers; glycerol esters, trialkyl citrates having a free or carboxylated OH group and having alkyl moieties of from 4 to 10 carbon atoms, and also alkyl benzoates, preferably having from 7 to 13 carbon atoms in the alkyl chain. In all cases, the alkyl moieties can be linear or branched and identical or different.

The composition particularly preferably comprises, alongside diisononyl terephthalates, in particular an alkyl benzoate having from 7 to 13 carbon atoms in the alkyl moiety, preferably isononyl benzoate, nonyl benzoate, isodecyl benzoate or decyl benzoate, or 2-propylheptyl benzoate. Particular preference is likewise given to a mixture composed of diisononyl terephthalates with dipentyl terephthalates.

The proportion of inventive diisononyl terephthalates in the mixture with other plasticizers is preferably from 15 to 95%, particularly preferably from 20 to 90% and very particularly preferably from 25 to 85%, where the proportions by weight of all of the plasticizers present give a total of 100%.

The compositions mentioned composed of diisononyl terephthalate and of other plasticizers can be used as plasticizer composition in plastics and plastics compositions, in adhesives, in sealing compositions, in coatings, in paints, in plastisols, or in inks.

The inventive plastics compositions which comprise the diisononyl terephthalate mixtures according to the invention can be polymers selected from polyvinylchloride (PVC), polyvinylidene chloride (PVDC), polyacrylates, in particular polymethyl methacrylate (PMMA), polyalkyl methacrylate (PAMA), fluoropolymers, in particular polyvinylidene fluoride (PVDF), polytetrafluoroethylene (PTFE), polyvinyl acetate (PVAc), polyvinyl alcohol (PVA), polyvinyl acetals, in particular polyvinyl butyral (PVB), polystyrenepolymers, in particular polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid-copolymer, polyolefins, in particular polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, in particular polylactic acid (PLA), polyhydroxybutyric acid (PHB), polyhydroxyvaleric acid (PHV), polyester, starch, cellulose and cellulose derivatives, in particular nitrocellulose (NC), ethylcellulose (EC), cellulose acetate (CA), cellulose acetate/butyrate (CAB), rubber or silicones, and also mixtures or copolymers of the polymers mentioned or of their monomeric units. The inventive compositions preferably comprise PVC or homo- or copolymers based on ethylene, on propylene, on butadiene, on vinyl acetate, on glycidyl acrylate, on glycidyl methacrylate, on methacrylates, on acrylates, or on acrylates or methacrylates having, bonded to the oxygen atom of the ester group, alkyl moieties of branched or unbranched alcohols having from one to ten carbon atoms, or on styrene, on acrylonitrile, or on cyclic olefins.

The inventive composition in the form of a grade of PVC preferably comprises suspension PVC, bulk PVC, microsuspension PVC or emulsion PVC. Based on 100 parts by weight of polymer, the inventive compositions preferably comprise from 5 to 200, with preference from 10 to 150, parts by weight of inventive plasticizer.

The inventive compositions can comprise, alongside the constituents mentioned, further constituents, for example in particular further plasticizers, fillers, pigments, stabilizers, co-stabilizers, such as epoxidized soybean oil, lubricants, blowing agents, kickers, antioxidants or biocides.

The inventive compositions composed of diisononyl terephthalates and of the abovementioned polymer materials can be used as plastics compositions, adhesives, sealing compositions, coatings, paints, plastisols, synthetic leather, floor coverings, underbody protection, textile coatings, wallpapers or inks, or for the production of these.

Examples of plastics products produced using the plasticizer compositions can be: profiles, gaskets, food-or-drink packaging, foils, toys, medical items, roof sheeting, synthetic leather, floor coverings, underbody protection, coated textiles, wallpapers, cables and wire sheathing. Preferred application sectors from this group are food-or-drink packaging, toys, medical items, wallpapers and floor coverings.

The examples below are intended to illustrate the invention, which is not restricted thereto.

EXAMPLES

Example 1

Inventive

Production of Diisononyl Terephthalate (DINTP) from Terephthalic Acid and Isononanol from Evonik OXENO Olefinchemie 830 g (5 mol) of terephthalic acid (Sigma Aldrich), 2.08 g (0.25% by weight, based on terephthalic acid) of tetrabutyl orthotitanate and 1800 g (12.5 mol) of an isononanol produced by the OCTOL process (Evonik OXENO Olefinchemie) were used as initial charge in a 4-litre stirred flask with distillation bridge with reflux divider, 20 cm multifill column, stirrer, immersed tube, dropping funnel and thermometer, and were esterified at 230° C. After 9 hours, the reaction had ended, and then the excess alcohol was removed by distillation at 180° C. and 3 mbar. The system was then cooled to 80° C. and neutralized using 6 ml of a 10% strength by weight aqueous NaOH solution. Steam distillation was then carried out at a temperature of 180° C. and at a pressure of from 20 to 5 mbar. The mixture was then dried at this temperature at 5 mbar and filtered after cooling to 120° C. GC showed 99.9% ester content.

The degree of branching of the alcohol side chain of this ester was determined as XX.

The glass transition temperature (DIN "average") was determined by differential scanning calorimetry (DSC) as −83° C. No melting signals were detected.

The product can therefore be used without difficulty as plasticizer in plastisols, as shown by example 6.

Example 2

Inventive

Production of DINTP from Dimethyl Terephthalate (DMT) and Isononanol 388 g (2 mol) of DMT (Oxxynova), 1.16 g (0.3% by weight, based on DMT) of tetrabutyl orthotitanate and initially 288 g of a total of 720 g (5 mol) of isononanol (Evonik OXENO) were used as initial charge in a 2-litre stirred flask with distillation bridge with reflux divider, 20 cm multifill column, stirrer, immersed tube, dropping funnel and thermometer. The system was slowly heated until all solid had disappeared and then the stirrer was switched on. The system was further heated until methanol appeared at the reflux divider. The reflux divider was adjusted to keep the overhead temperature constant at about 65° C. Starting at a temperature of about 230° C. at the bottom of the column, the remainder of the alcohol was slowly run in such a way as to avoid lowering the temperature in the flask below 220° C. and to retain adequate reflux. At intervals, a specimen was studied by GC and the content of diisononyl terephthalate was determined. The transesterification process was stopped when the content of diisononyl terephthalate was 99.8%.

Example 3

Inventive

Production of DINTP from Terephthalic Acid and Isononanol from ExxonMobil 830 g (5 mol) of terephthalic acid (Sigma Aldrich), 2.08 g (0.25% by weight, based on terephthalic acid) of tetrabutyl orthotitanate and 1728 g (12 mol) of an isononanol from the polygas process (Exxal 9, ExxonMobil) were used as initial charge in a 4-litre stirred flask with distillation bridge with reflux divider, 20 cm multifill column, stirrer, immersed tube, dropping funnel and thermometer, and were esterified at 245° C. After 10.5 hours, the reaction had ended, and then the excess alcohol was removed by distillation at 180° C. and 3 mbar. The system was then cooled to 80° C. and neutralized using 12 ml of a 10% strength by weight aqueous NaOH solution. Steam distillation was then carried out at a temperature of 180° C. and at a pressure of from 20 to 5 mbar. The mixture was then dried at this temperature at 5 mbar and filtered after cooling to 120° C. GC showed 99.9% ester content.

The glass transition temperature (DIN average) was determined by DSC as −76° C.

The degree of branching of the alcohol side chain of this ester was determined as XX.

The relatively high degree of branching of the alcohol used here is therefore itself sufficient to increase the glass transition temperature of the corresponding ester significantly, and thus also to increase its capability of reducing the glass transition temperature of the PVC to the extent that it remains flexible even at relatively low outdoor temperatures.

Example 4

Comparative Example

Production of DINTP from Terephthalic Acid and n-Nonanol

By analogy with example 1, n-nonanol (FLUKA) was esterified with terephthalic acid and worked up as described above. When the product, whose ester content according to GC is >99.8%, is cooled to room temperature it solidifies.

The melting point was determined by DSC as 46° C., the incipient rise of the melting signal ("Onset") being utilized for this purpose. No glass transition temperature was detected.

Example 5

Comparative Example

Production of DINTP from Terephthalic Acid and 3,5,5-trimethylhexanol

By analogy with example 1,3,5,5-trimethylhexanol (FLUKA) was esterified with terephthalic acid and worked up as described above. When the product, whose ester content according to GC is >99.5%, is cooled to room temperature it solidifies.

When melting point was determined by DSC, two melting signals were detected. The incipient rise in the curve ("Onset") of the lower of the two is at 42° C. No glass transition temperature was detected.

Example 6

Production of Plastisols

A plastisol was produced as follows using the inventive diisononyl terephthalate produced according to example 1:

100 g of the dinonyl terephthalate, 6 g of epoxidized soybean oil (DRAPEX 39) and 3 g of Ca/Zn stabilizer (MARK CZ 140) were first weighed into a PE beaker, and then 200 g of PVC (Vestolit B 7021) were added. The temperature of each of the liquids had been controlled in advance to 25° C. The mixture was stirred manually with a paste spatula until all of the powder had been wetted. The mixing beaker was then clamped into the clamping equipment of a dissolver mixer. Prior to immersion of the stirrer into the mixture, the rotation rate was set at 1800 revolutions per minute. Once the stirrer had been switched on, stirring was continued until the temperature on the digital display of the temperature sensor reached 30.0° C. This ensured that the plastisol was homogenized with defined energy input. The temperature of the plastisol was then immediately controlled to 25.0° C.

Example 7

Measurement of Viscosity of Plastisol

The viscosities of the plastisol produced in example 6 were measured by analogy with DIN 53 019 using a Physica DSR 4000 Rheometer (Paar-Physica), controlled by way of the associated US 200 software, using the following method:

The plastisol was again stirred with a spatula in the storage container and tested in the Z3 test system (DIN 25 mm) according to the operating instructions. The test proceeded automatically by way of the above-mentioned software at 25° C. The following conditions were applied:

pre-shear of 100 $s^{-1}$ for a period of 60 s without recording any test values a downward gradient starting at 200 $s^{-1}$ and extending downward as far as 0.1 $s^{-1}$, divided into a logarithmic series with 30 steps with in each case a measurement point duration of 5 s.

The test data were automatically processed by the software after the test. Viscosity was shown as a function of shear rate. The test was carried out after a storage period of 2 hours in standard conditions of temperature and humidity.

Graph 1 shows the viscosity of the plastisol as a function of shear rate.

From this, it is readily clear to the person skilled in the art that the plastisol has good processability, since the viscosities of the plastisol in the central shear rate range (10 $s^{-1}$) are relatively low and the incipient rise in the higher range of shear rate is relatively moderate.

The invention claimed is:

1. A mixture, comprising:
   diisononyl esters of terephthalic acid, comprising isomeric nonyl moieties,
   wherein an average degree of branching of the isomeric nonyl moieties of the esters in the mixture is from 1.0 to 2.2, and
   having a glass transition temperature below −70° C.

2. The mixture of claim 1, wherein the average degree of branching of the isomeric nonyl moieties of the esters in the mixture is from 1.1 to 2.1.

3. The mixture of claim 1, wherein the average degree of branching of the isomeric nonyl moieties of the esters in the mixture is from 1.1 to 2.0.

4. The mixture of claim 1, wherein the average degree of branching of the isomeric nonyl moieties of the esters in the mixture is from 1.2 to 1.5.

5. The mixture of claim 1, wherein the isomeric nonyl moieties of the esters in the mixture comprise primary nonyl alcohols.

6. A process for the production of the mixture of claim 1, comprising:
   esterifying terephthalic acid or a terephthalate with a mixture of isomeric nonanols whose average degree of branching is from 1.0 to 2.2.

7. The process of claim 6, wherein the esterifying comprises a transesterification of terephthalic esters, comprising alkyl moieties which comprise fewer than 8 carbon atoms, with a mixture of isomeric primary nonanols.

8. The process of claim 6, wherein the esterifying comprises an esterification of terephthalic acid with a mixture of primary nonanols.

9. The process of claim 6, wherein the esterifying comprises a complete or partial transesterification of a dinonyl terephthalate or of a mixture of isomeric dinonyl terephthalates, with a primary nonanol or a mixture of primary nonanols.

10. The process of claim 6, wherein the esterifying comprises:
    mixing isomerically pure nonyl terephthalates with one another,
    mixing an isomerically pure nonyl terephthalate with a mixture of nonyl terephthalates, or
    mixing two or more mixtures of dinonyl terephthalates.

11. The process of claim 6, wherein the mixture of isomeric nonanols comprises from 0.0001 to 10 mol % of 3,5,5-trimethylhexanol.

12. The process of claim 11, wherein the mixture of isomeric nonanols comprises less than 5 mol % of 3,5,5-trimethylhexanol.

13. The process of claim 6, wherein a proportion of n-nonanol in the isomeric nonanols mixture is from 0.001 to 20 mol %.

14. A process of manufacturing a plastic or a component of plastic, comprising:
    adding a plasticizer comprising the mixture of claim 1 to a plastic or a component of plastic.

15. A plastic or plastics composition, comprising the mixture of claim 1.

16. A PVC, PVB, or PAMA composition, or a plastics product produced from the PVC, PVB, or PAMA composition, comprising:
    the mixture of claim 1.

17. The mixture of claim 1, wherein a proportion of 3,5,5-trimethylhexanol in the isomeric nonyl moieties of the mixture is less than 1 mol %.

18. The mixture of claim 1, wherein a proportion of n-nonanol in the mixture is less than 2 mol %.

19. The mixture of claim 1, having a glass transition temperature below −80° C.

* * * * *